United States Patent [19]

Ross et al.

[11] Patent Number: 5,318,543

[45] Date of Patent: Jun. 7, 1994

[54] LAPAROSCOPIC JEJUNOSTOMY INSTRUMENTATION KIT

[75] Inventors: Jeffrey R. Ross, Dublin; Mark A. McCamish, Worthington; Andrea L. Senokozliff-Englehart, Columbus; Roger G. Danis, Westerville, all of Ohio

[73] Assignee: Abbott Laboratories, Abbott Park, Ill.

[21] Appl. No.: 958,409

[22] Filed: Oct. 8, 1992

[51] Int. Cl.[5] ............................................. A61M 5/00
[52] U.S. Cl. .................................. 604/164; 604/174; 604/175; 604/264; 206/571
[58] Field of Search .................. 604/51, 54, 158, 160, 604/161, 164, 178, 264, 280, 174; 606/108, 191; 206/364–366, 571

[56] References Cited

U.S. PATENT DOCUMENTS

| | | | |
|---|---|---|---|
| Re. 34,021 | 8/1992 | Mueller et al. ................. | 604/51 |
| 4,261,363 | 4/1981 | Russo ............................. | 604/174 |
| 4,573,576 | 3/1986 | Krol .............................. | 604/280 |
| 4,705,040 | 11/1987 | Mueller et al. .................. | 604/51 |
| 4,834,712 | 5/1989 | Quinn et al. .................... | 604/174 |
| 5,112,310 | 5/1992 | Grobe ............................ | 604/164 |
| 5,139,486 | 8/1992 | Moss .............................. | 604/158 |
| 5,144,942 | 9/1992 | Decarie et al. .................. | 128/4 |
| 5,151,086 | 9/1992 | Duh et al. ...................... | 604/51 |
| 5,158,543 | 10/1992 | Lazarus ......................... | 604/164 |
| 5,167,627 | 12/1992 | Clegg et al. .................... | 604/164 |

OTHER PUBLICATIONS

Sandoz Nutrition Sales Literature for "The NUPORT® PEG".

*Primary Examiner*—C. Fred Rosenbaum
*Assistant Examiner*—Anthony Gutowski
*Attorney, Agent, or Firm*—Lonnie R. Drayer; Donald O. Nickey

[57] ABSTRACT

A laparoscopic jejunostomy instrumentation kit includes components for securing a patient's intestine in apposition to the patient's abdominal wall and for creating a stoma through the patient's abdominal wall and intestinal wall, a jejunostomy tube, and an enclosure for containing the other components of the kit. In preferred embodiments the kit includes T-Fastener assemblies, needles, syringes, a dilator, a peel-away sheath and a gastrostomy tube.

5 Claims, 12 Drawing Sheets

LAPAROSCOPIC JEJUNOSTOMY INSTRUMENTATION KIT

FIELD OF THE INVENTION

The present invention relates to laparoscopic surgical instruments and gastrostomy tubes, and more particularly to a kit for packaging laparoscopic surgical instruments and jejunostomy tubes for use during a surgical procedure.

BACKGROUND OF THE INVENTION

A surgical procedure wherein an opening is formed in the skin, fascia and jejunal wall, and a tube is installed in the opening to allow nutrition to be provided directly into the intestine is known as a jejunostomy. A tube which is inserted through this opening during the surgical procedure to maintain the opening is known as a jejunostomy tube. Examples of individuals who would require such a procedure include patients who are poor candidates for nasoenteric or gastrostomy tube feedings, patients whose daily caloric needs are very high; critically ill, weak or comatose patients who may be unable to chew food, and patients suffering from a diseased or traumatized esophagus, who may be unable to swallow food.

A relatively new method of placing a jejunostomy tube, which is described in U.S. Pat. No. 5,151,086 relates to a laparoscopic procedure. Laparoscopic surgery generally requires the use of instruments or equipment which provides a passage through the skin and surrounding tissue to the surgical site. The laparoscopic jejunostomy procedure requires the use of many instruments and supplies including for example, a nasogastric tube, scalpel, needles, syringes, T-Fastener assemblies, a J-Guidewire, a dilator, a peel-away sheath, a jejunostomy tube and water-soluble lubricant.

In view of this, it is required that assistants to the surgical procedure prepare for the operation by making ready these numerous instruments and supplies to aid in the performance of the surgical procedure. To this end, the individual packaging of each of these items leads to the accumulation of packaging material within the sterile environment of the operating room. It is also conceivable that certain necessary pieces of operating equipment and instrumentation will be inadvertently omitted from the operating room, thus delaying the turgical procedure or inconveniencing the surgeon and jeopardizing the safety of the patient.

The novel laparoscopic jejunostomy instrumentation kit of the present invention obviates the disadvantages encountered in the prior art and provides an instrumentation kit which may include all the necessary pieces of equipment required for performing this surgical procedure. The amount of packaging material which must be discarded is significantly reduced, and the possibility of omission of a required piece of equipment is essentially eliminated.

BRIEF DESCRIPTION OF THE DRAWINGS

The features of the present invention which are believed to be novel are set forth with particularity in the appended claims. The present invention, both as to its structure and manner of operation, may best be understood by referring to the following detailed description, taken in accordance with the accompanying drawings in which:

DETAILED DESCRIPTION OF THE INVENTION

Figure 1:
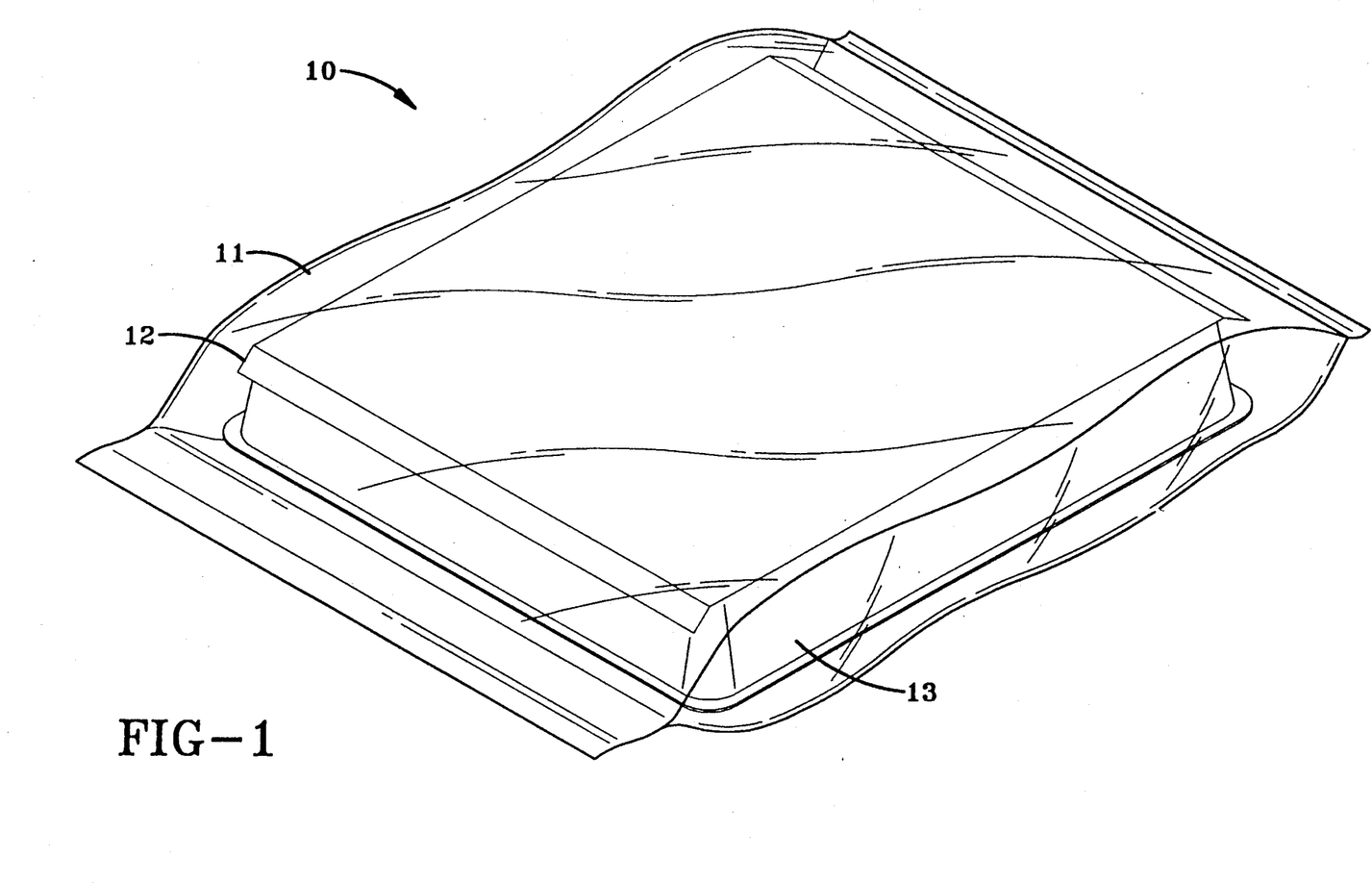
FIG. 1 is a pictorial representation of an unopened laparoscopic jejunostomy instrumentation kit contained in a sealed wrapper.

Referring first to FIG. 1, there is shown a laparoscopic jejunostomy instrumentation kit 10 which comprises a sealed clear plastic wrapper 11 which encloses a label or drape 12 which overlies a tray 13 which contains instruments and supplies which are necessary for performing a laparoscopic jejunostomy procedure.

Figure 2:
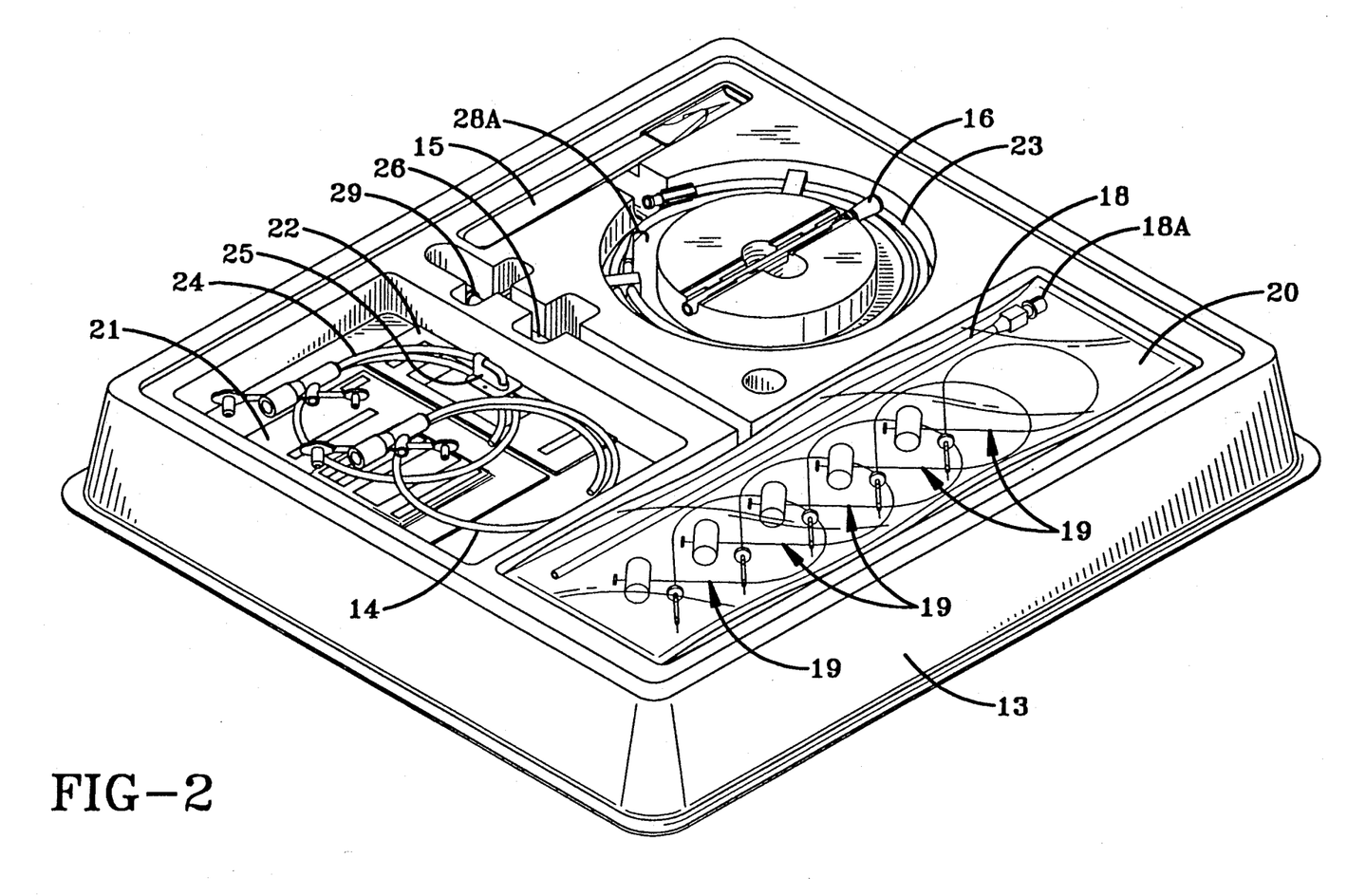
FIG. 2 and 3 are pictorial representations of the laparoscopic jejunostomy instrumentation kit with the wrapping removed, showing he contents of the kit.

Referring next to FIG. 2 the kit is shown with the plastic wrapper and label or drape removed. The tray 13 is made of a formed plastic which is capable of withstanding an appropriate sterilization process. The tray may be, for example, vacuum formed. Preferably, the tray provides recesses which correspond in dimension and shape to the various components of the kit packaged therein, which serve to retain the components of the kit while displaying them for the surgical staff.

Figure 3:
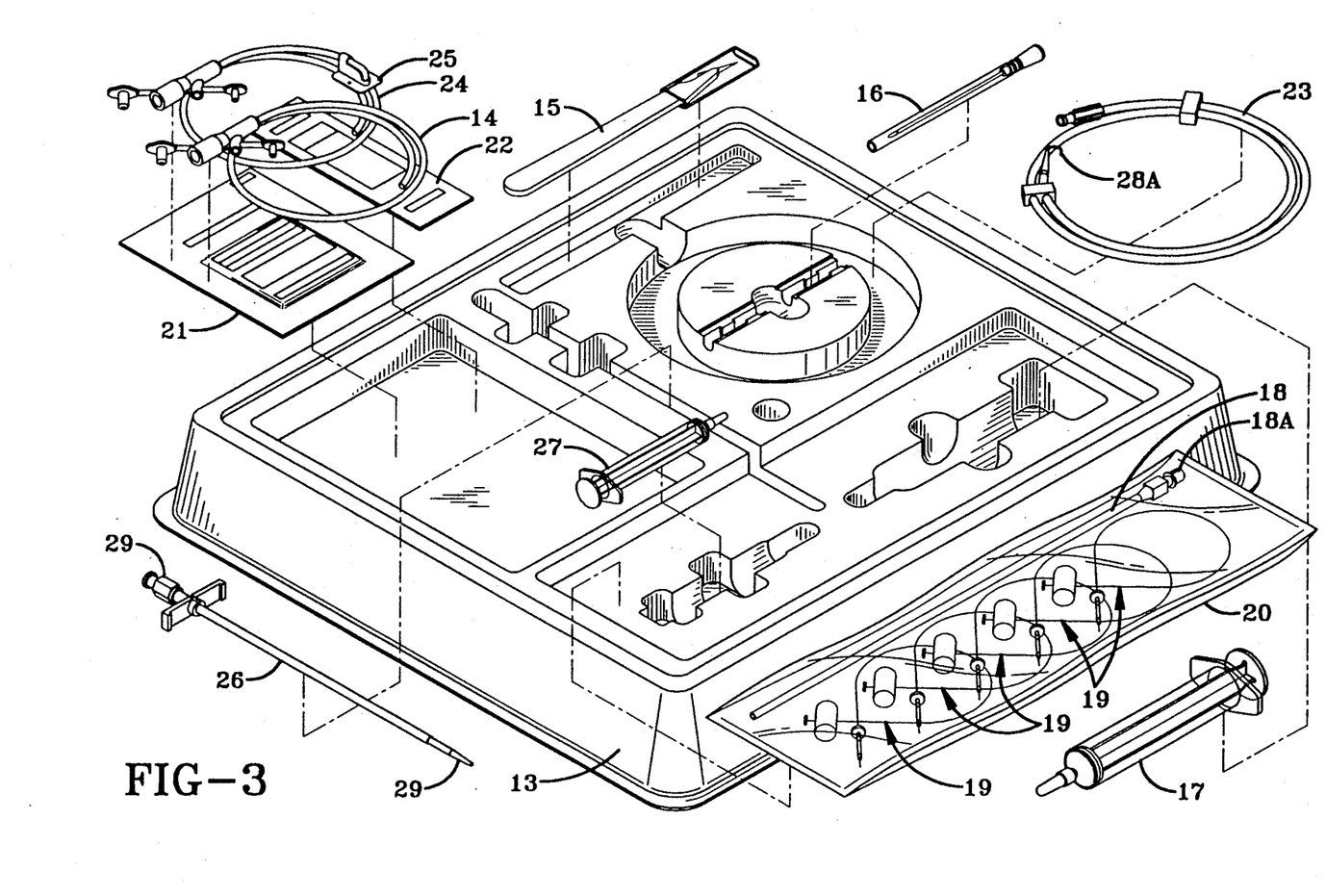

Referring next to FIGS. 2 and 3 the components of the kit which are packaged in the tray 13 are illustrated. A nasogastric tube 14, a jejunostomy tube 24 with an external retaining device 25, and a packet of water-soluble lubricant 22 are disposed within a first recess in the tray 13. Generally, the jejunostomy tube 24 comprises a hollow shaft, having a Y-port located at one end of the shaft. It is understood that optional additional kit components such as a sterile drape, swabs, a packet of cotton gauze squares 21 and so forth could also be placed in this recess if desired. A 5 cc syringe 27, a 20 cc syringe 17 and a #11 scalpel 15 are each located in individual recesses in the secondary tray 13. The syringes may be conveniently used by the surgeon for a variety of purposes such as inserting air, aspirating, or administering a drug such as lidocaine. While it is contemplated that only one syringe is needed to perform the surgical procedure, two syringes may be included in the instrumentation kit at the option of the manufacturer and user. An 18 Ga by 2¾" long needle 16 and a J-Guidewire 23 are placed in another recess in the tray 13. It is to be noted that both the 18 Ga needle and the J-Guidewire are at least partially disposed within protective sheaths. The J-Guidewire comprises a core wire having a second wire helically wrapped thereabout, with a flexible J-Hook 28A disposed at one end thereof. However, it is understood that any suitable guidewire may be employed as a component of the instrumentation kit. The guidewire is of a size such that it is insertable through a bore in the 18 Ga needle.

Figure 4:
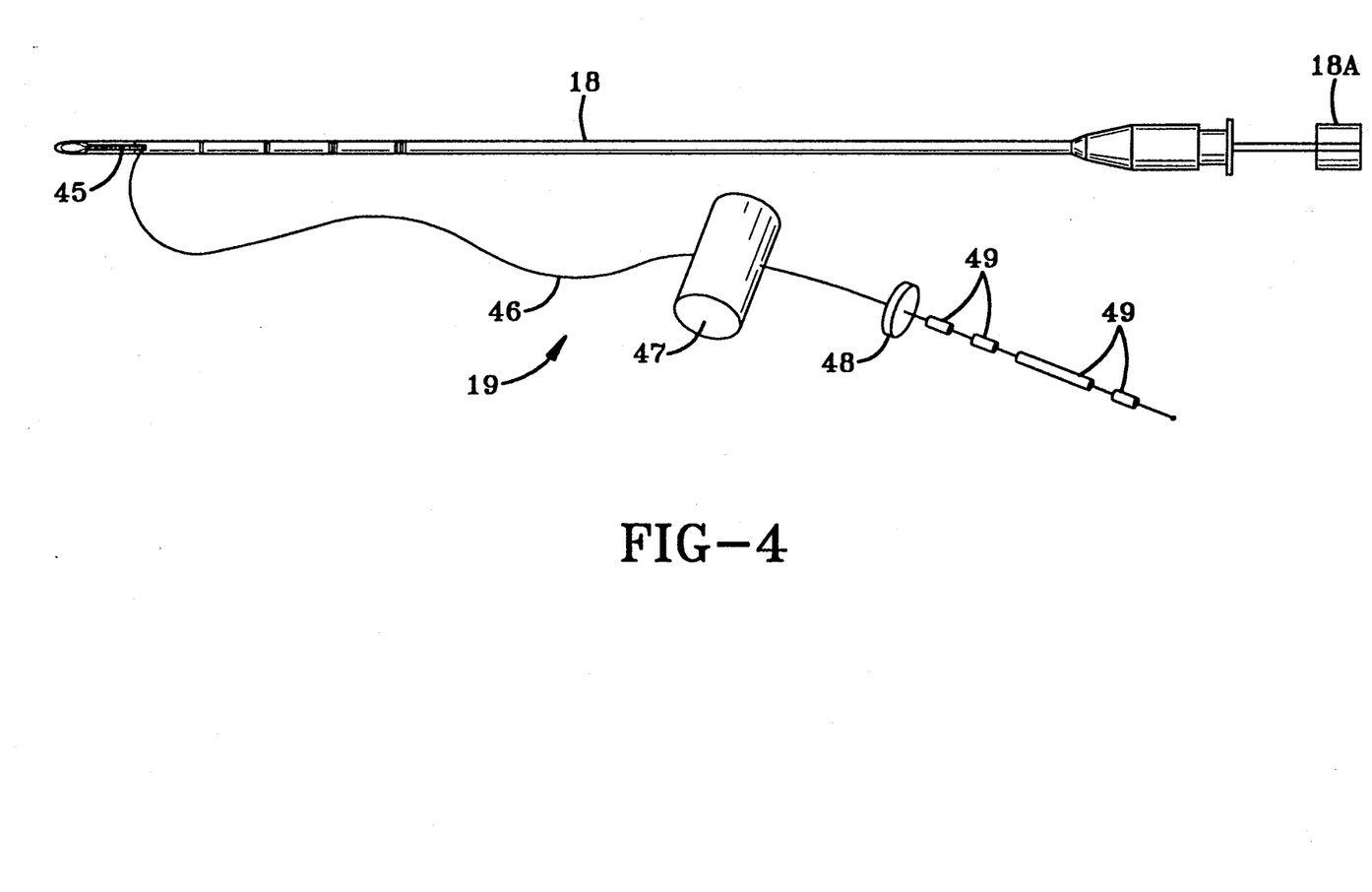
FIG. 4 is a pictorial representation of a T-Fastener assembly loaded into slotted needle.

A T-Fastener set comprising a slotted needle 18, stylet 18A, and five T-Fastener assemblies 19 packaged in a sealed pouch 20 is disposed in yet another recess in the tray 13. It should be noted that the shaft of the slotted needle 18 is disposed within a protective sheath in FIGS. 2 and 3. The T-Fasteners and their use are taught in commonly owned U.S. Pat. Re. 34,021 entitled PERCUTANEOUS FIXATION OF HOLLOW ORGANS which is incorporated herein by reference for the purpose of teaching in detail the structure and use of the T-Fasteners. However, the structure and use of the T-Fastener kit may be briefly described by referring to FIG. 4. The slotted needle 18 has a sharp tip, a longitudinal slot associated with the tip, a length suitable to permit percutaneous insertion, and an internal diameter large enough to accept the head of a "T" 45 so that the head of a "T" element is entirely within the needle when the needle is thrust through the flesh and the stomach wall. Also, as shown, the slotted needle has indicia located on its outer surface to indicate the depth of insertion of the needle. A stylet 18A is placed within the needle with one end near or touching the head of the "T" element and the other end extending through the hub of the needle. The head of the "T" 45 is preferably an elongated stainless steel cylinder, which is affixed to one end of a suture 46, which is preferably formed of nylon. As used herein and in the claims a T-Fastener assembly is understood to be an appropriate assembly of devices prearranged along a suture 46 for applying traction and securing the "T" element in place, preferably comprising a cylindrical member 45, a compressible pledget 47, a compression—applying retention disc or washer 48 to bear against the pledget and a crimpable clamping element 49 for permanently clamping the suture and applying compression to the compression disc or washer 48. The pledget 47 is preferably formed of a soft, absorbent material such as cotton or methylcellulose, and acts as a cushion against the skin and as an absorbent for fluids. The compression applying tension disc or washer 48 is preferably formed of nylon, and the crimpable clamping devices 49 are preferably formed of aluminum.

As shown in FIG. 3, an assembly comprising a peel-away sheath 26 has a bore therethrough and a dilator 29 disposed within the bore in said peel-away sheath is located within yet another recess in the tray 13. The dilator 29 has a bore extending therethrough of a size large enough to accomodate insertion of the J-Guidewire. The bore through the peel-away sheath is large enough to allow the jejunostomy tube 24 to be passed therethrough following removal of the dilator.

While certain sizes have been specified for the various components of the kit, it is understood that such size designations are to be considered as merely illustrative, and that different sizes may be employed depending upon the contemplated patient, for example a child versus an adult.

The instrumentation kit of the present invention has utility in the performance if a laparoscopic jejunostomy surgical procedure, which is described below. Such a procedure is taught in U.S. Pat. No. 5,151,086.

The patient is prepared for laparoscopic surgery according to institutional standards, including the placement of a nasogastric tube 14. A skin incision is made inferior to the umbilicus. The subcutaneous tissue is spread using Kelly clamps.

A Veress needle is inserted into the peritoneal cavity at the incision site to insufflate the peritoneum. Correct placement of the Veress needle is confirmed by needle aspiration and syringe injection of saline. The aspiration of blood or bowel contents or injection requiring excessive pressure may indicate that the needle is not in the proper position. Needle placement is also confirmed by performing a drop test. Saline should infuse by gravity flow. If incorrect placement is confirmed, the needle is removed and a different site is selected. The peritoneum is insufflated to 15 mm Hg through the Veress needle. If abdominal distention is asymmetrical, this may provide an additional indication of improper Veress needle placement, requiring the removal of the needle and selection of a different site. After confirming proper placement and insufflation the Veress needle is removed and a trocar is placed in this site. A laparoscope is inserted and a diagnostic laparoscopy is performed.

The jejunum is insufflated via the previously placed nasogastric tube to improve jejunal access. Throughout the procedure assessments are made for jejunal deflation, and if necessary the jejunum is reinsufflated. Initiating and maintaining jejunal insufflation is critical to the procedure. Insufflation helps prevent inappropriate T-Fastener placement through the posterior jejunal wall. (Perforation of the posterior jejunal wall could result in peritonitis.)

The patient is placed in the right lateral reverse Trendelenburg position. The accessibility of the jejunum is laparoscopically ascertained. One or two trocars are placed as conduits for graspers which are used to manipulate the omentum and transverse colon to the upper part of the abdomen.

The location of the jejunostomy site is determined internally by identifying the proximal jejunum in the upper left quadrant of the abdomen. Using a grasper, the bowel is run to the Ligament of Treitz. The jejunostomy site is selected approximately 30 cm distal to this point. A site is chosen that will allow the bowel to be fixed to the abdominal wall without kinking. (Kinking the jejunum may obstruct it.)

Figure 5:
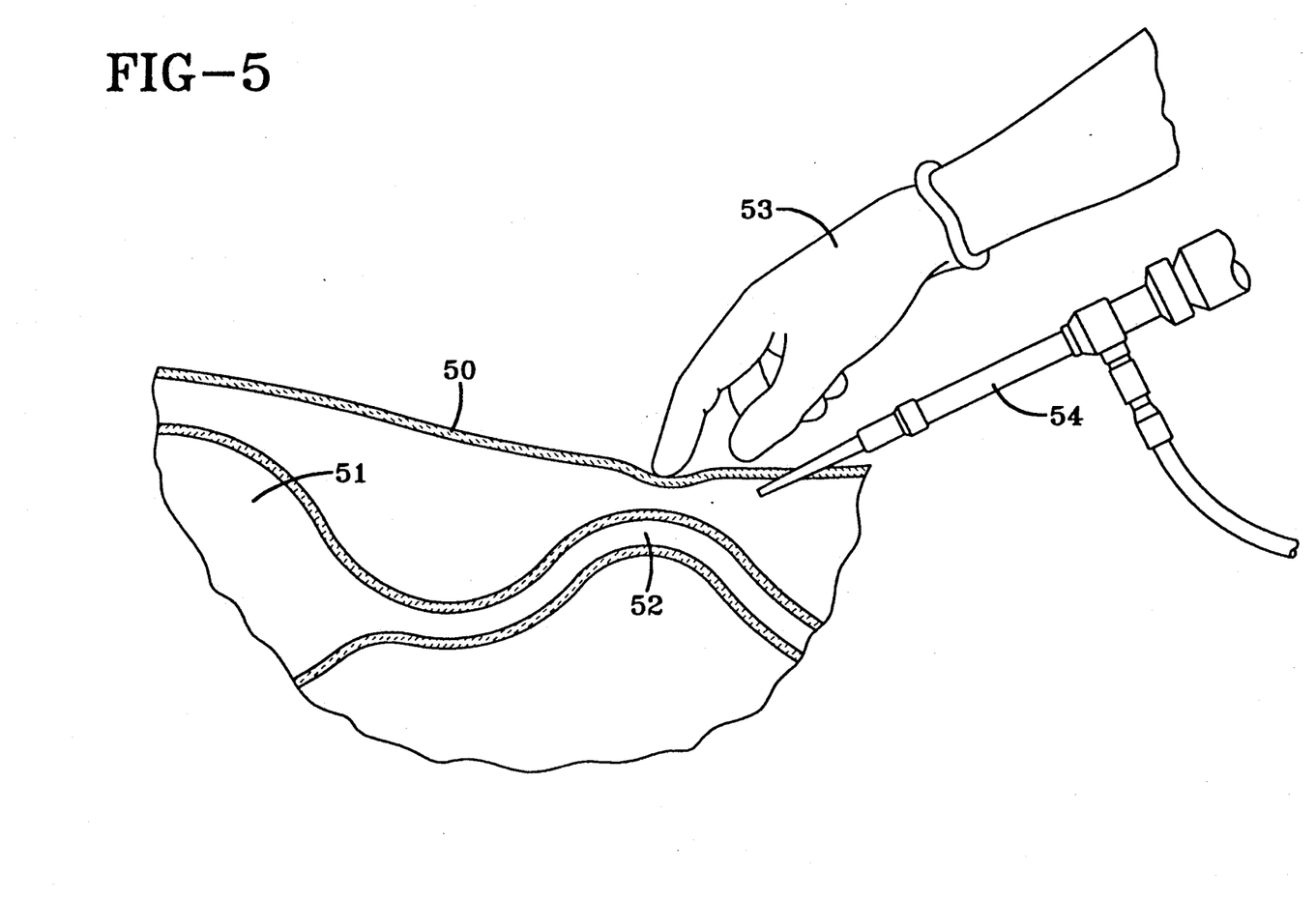
FIGS. 5 through 12 illustrate a laparoscopic jejunostomy procedure employing the instrumentation kit of the invention.

As shown in FIG. 5, the external jejunostomy site 52 is determined on the abdominal wall 50 by the surgeon exerting external finger pressure viewed internally through the laparoscope 54.

Figure 6:
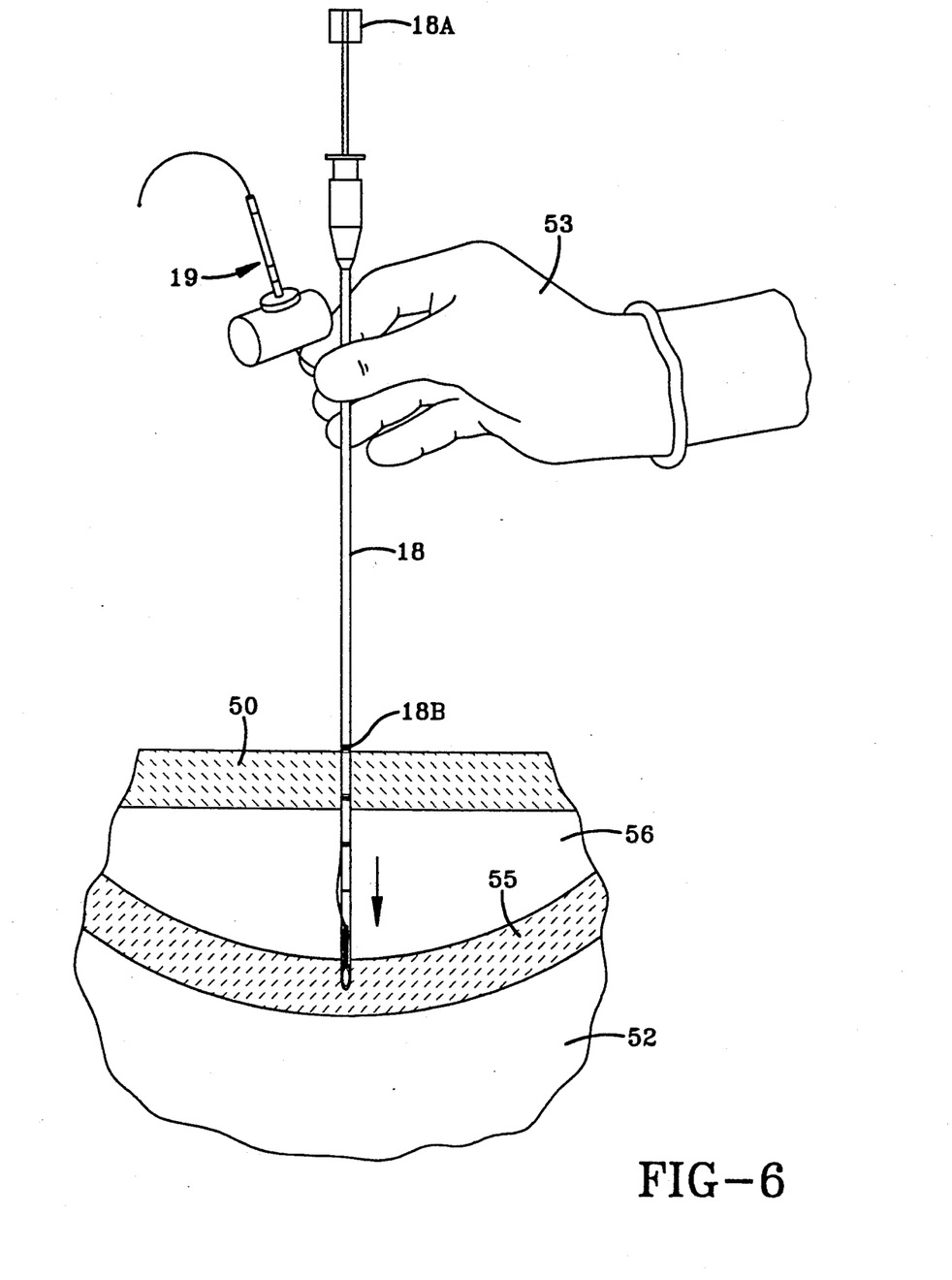
Figure 7:
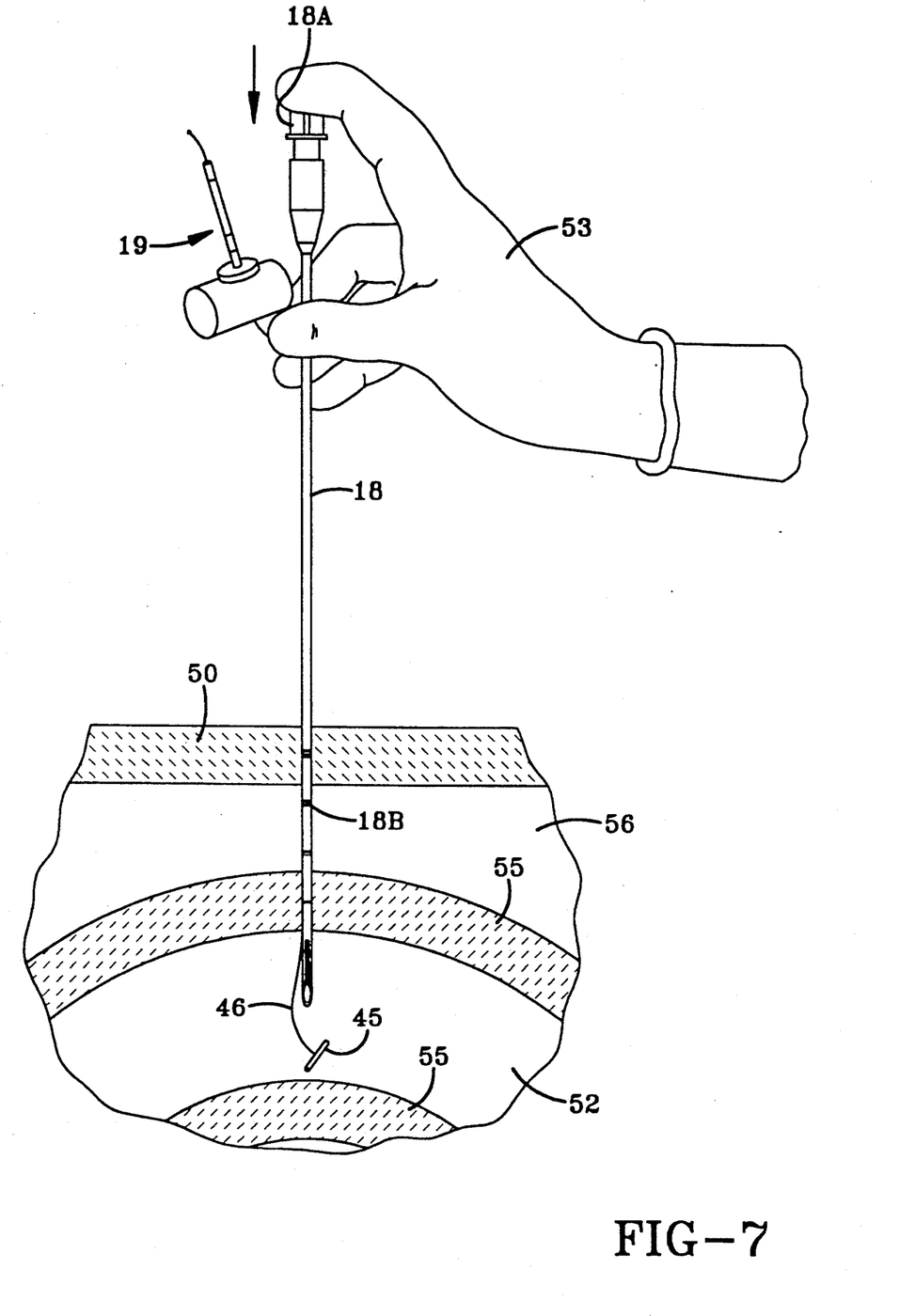

The T-Fasteners are then placed. The slotted needle is preloaded with a T-Fastener, assuring that the grommet is positioned at the proximal end of the stylet as described above with respect to FIG. 4. With reference to FIG. 6, the pneumoperitoneum is decreased to 7–10 mm Hg to allow the jejunum 52 to be drawn close to the anterior abdominal wall 50. The preloaded slotted needle 18 is inserted by the surgeon 53 with gentle, firm pressure through the most cephalad of the four T-Fastener sites and into the peritoneal cavity 56. (Eventually the T-Fasteners should form a two inch square pattern when properly placed.) The surgeon continues to insert the slotted needle with the loaded T-Fastener assembly 19 at a 45° angle through the jejunal wall 55 observing the centimeter markings 18B for estimation of penetration depth. Graspers are used to retract the bowel if needed. Through the T-Fastener placement extreme caution is taken not to penetrate the posterior jejunal wall, which could result in peritonitis. (If the bowel was difficult to insufflate the slotted needle without the stylet may be used for this purpose, with a quick injection of air confirming that the needle is in the lumen.) When the needle has advanced beyond the mucosal surface the resistance drops and the jejunal wall is no longer depressed by the needle. (If the needle has not penetrated the mucosa the "T" will not advance.) The grommet on the stylet 18A is depressed to dislodge the T-Fastener from the slot in the needle, as shown in FIG. 7.

Figure 8:
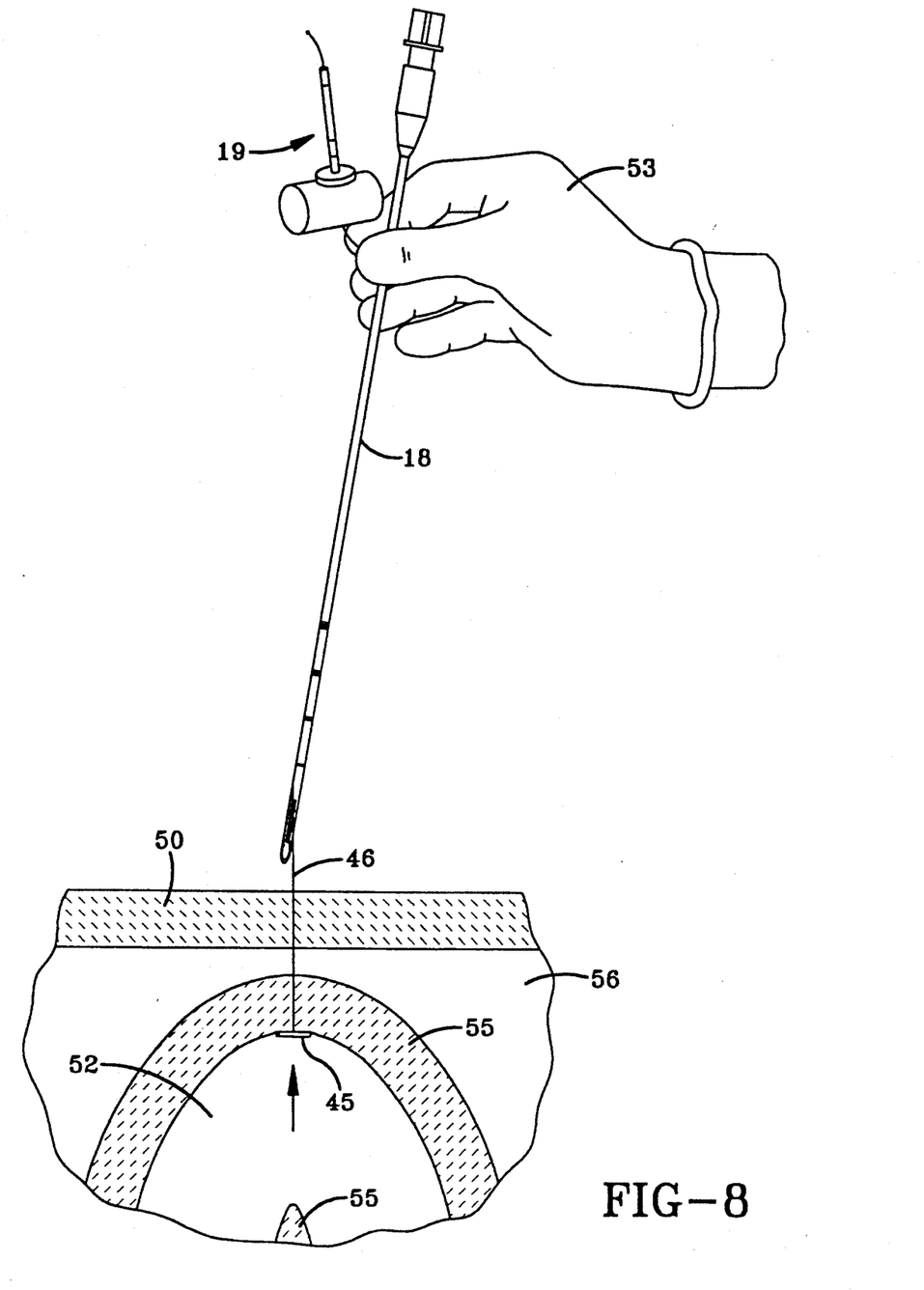

With reference to FIG. 8 the needle 18 and stylet 18A are withdrawn simultaneously, while the surgeon 53 continues to gently pull the "T" 45 until it is flush against the jejunal wall 55. Tension on the suture 46 is an indication that the head of the "T" is pulled against the jejunum. (Note that if the "T" is accidentally dislodged into the peritoneum, or penetrated the posterior jejunal wall, it can be retrieved by cutting the suture at the skin and then extracting the T-Fastener with a grasper. The spare fifth T-Fastener is used to replace the lost one.) Tension on the "T" is maintained while pulling it up to the anterior abdominal wall 50 until the "T" has deformed the jejunal wall upward. Some distance is maintained between the jejunal wall and the anterior abdominal wall so that each subsequent T-Fastener can be placed under direct vision. The jejunal wall is not pulled snug against the abdominal wall at this point because it would obscure the exposure needed to place the remaining T-Fasteners. The placement process is repeated for the three other T-Fasteners. After four T-Fasteners have been properly positioned in a square pattern, tension is placed on the sutures to snug the jejunum to the anterior abdominal wall. An assistant maintains tension on the sutures, or a clamp is used to maintain tension on the sutures, while creating the stoma tract and inserting the jejunostomy tube. The aluminum crimps of the T-Fasteners are not crimped at this point. (Note that while some surgeons may choose to use only three T-Fasteners in a triangular formation, this is not the recommended procedure and the safety of such a procedure has not been confirmed.)

Figure 9:
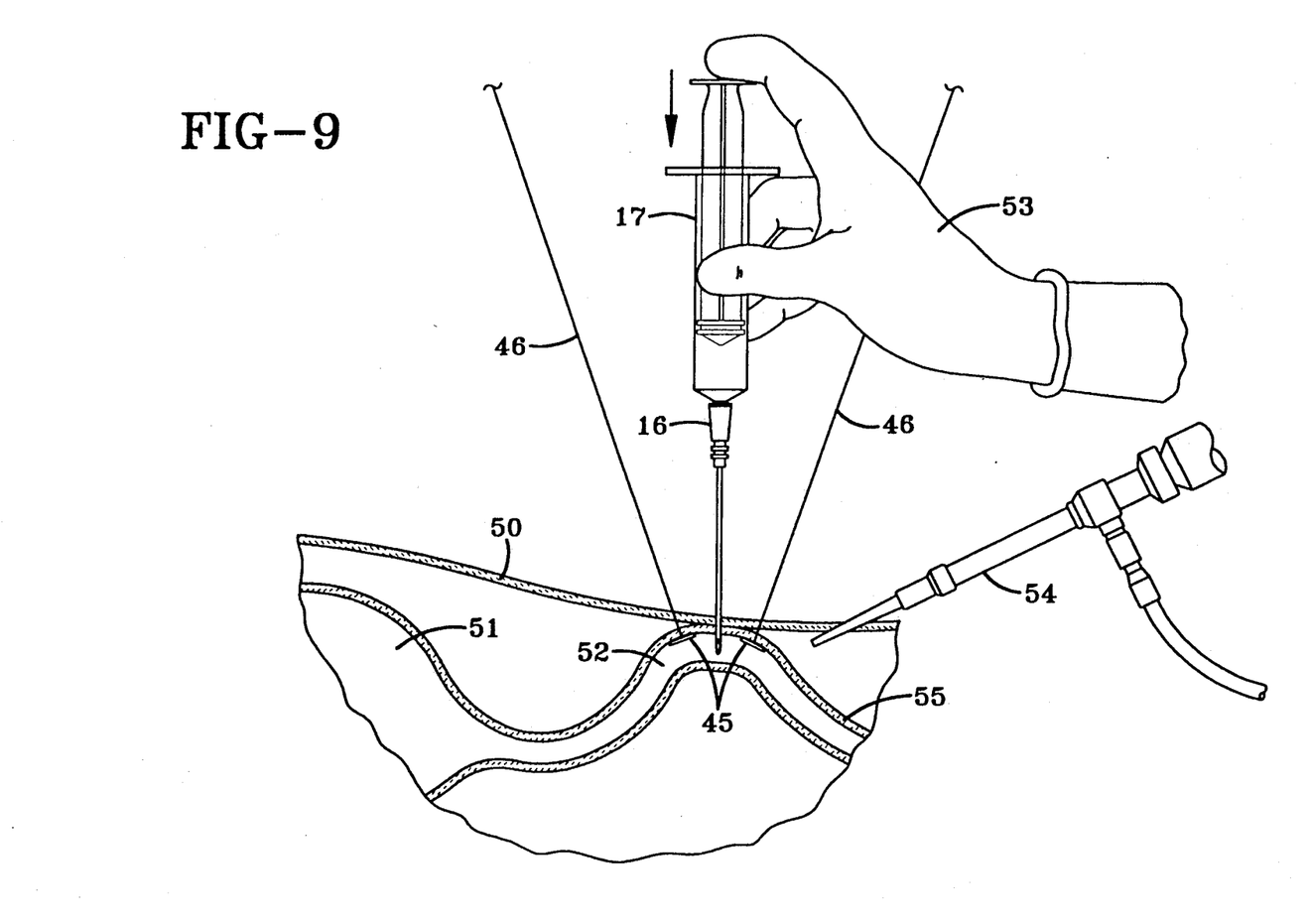
Figure 10:
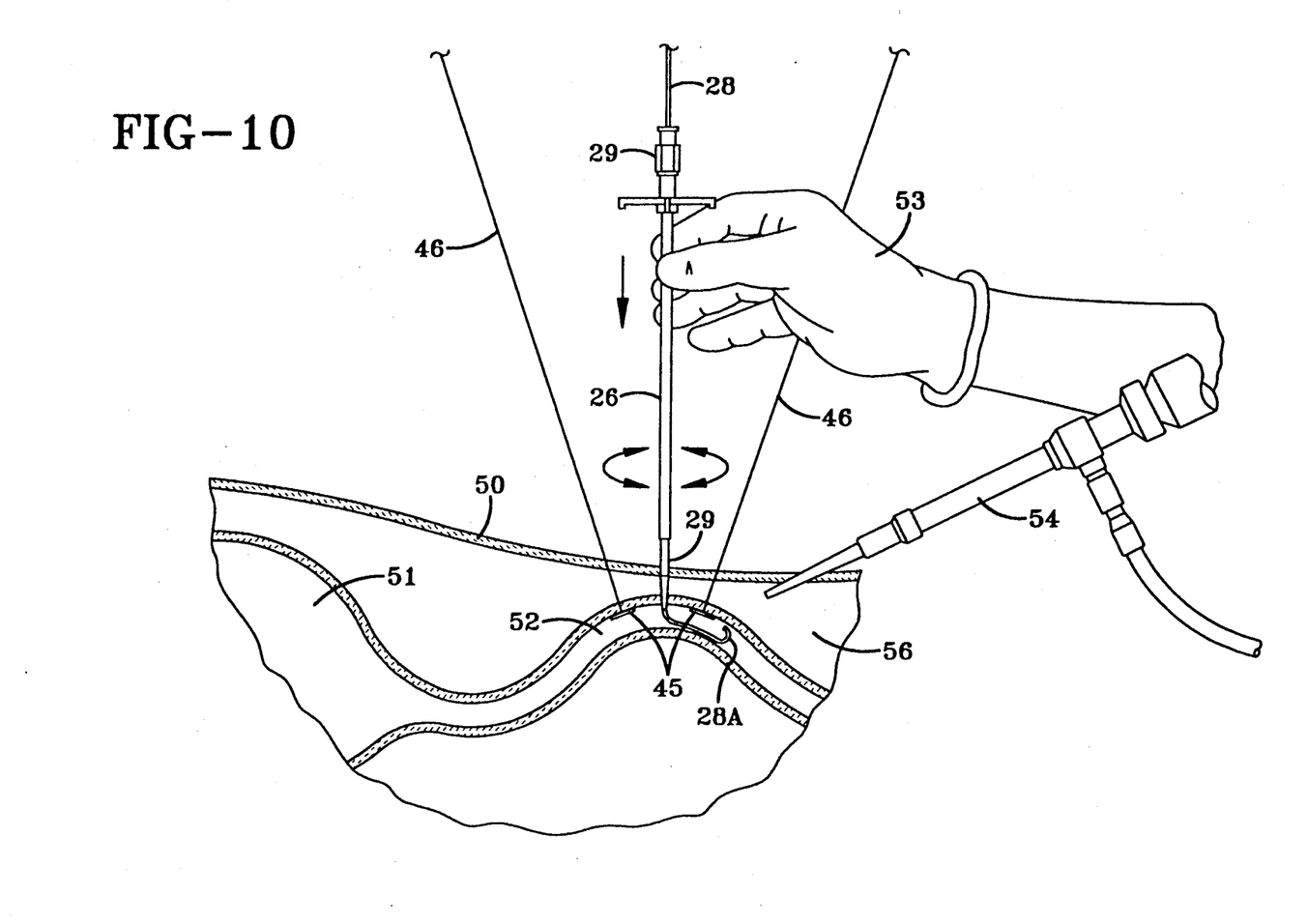
Figure 11:
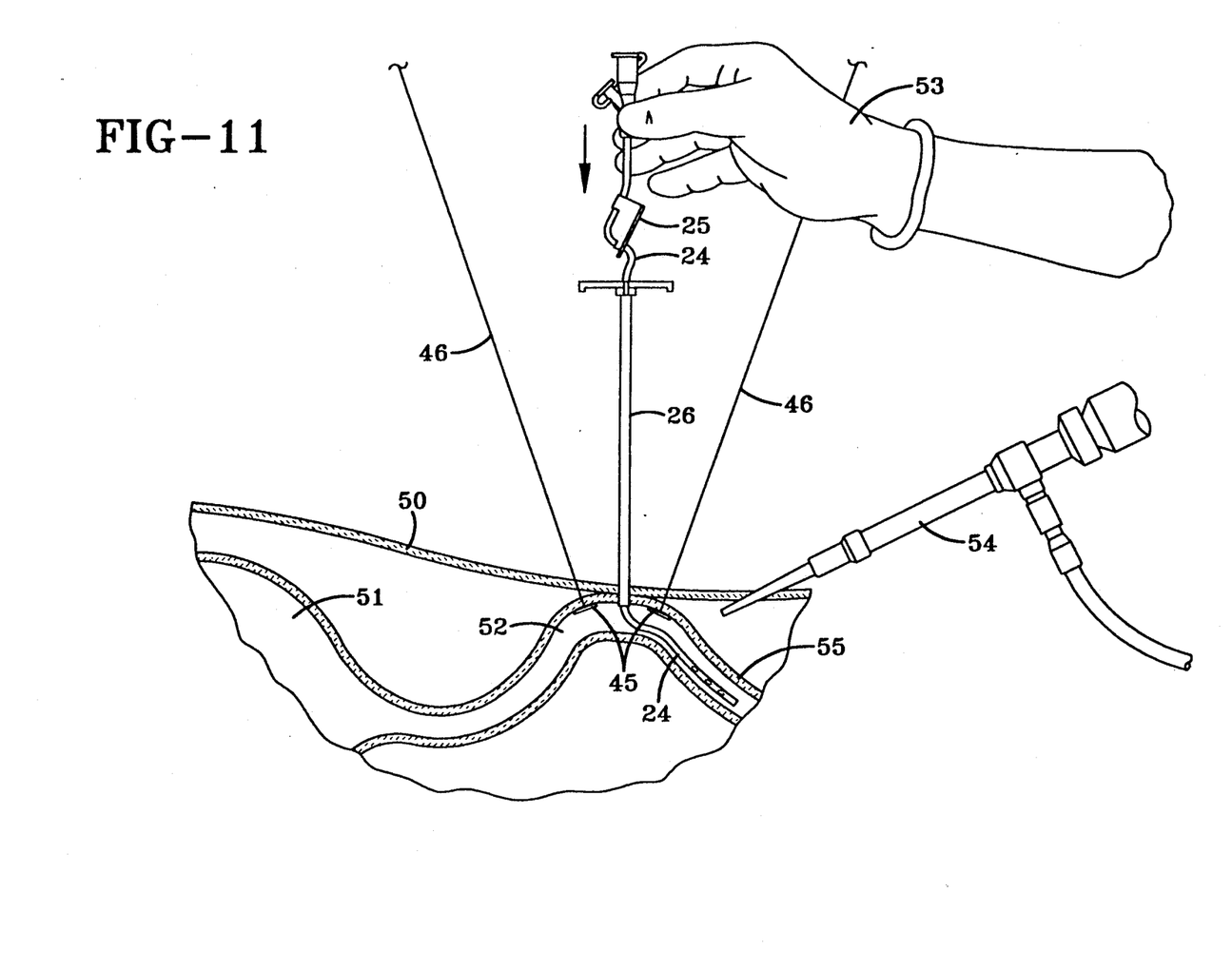
Figure 12:
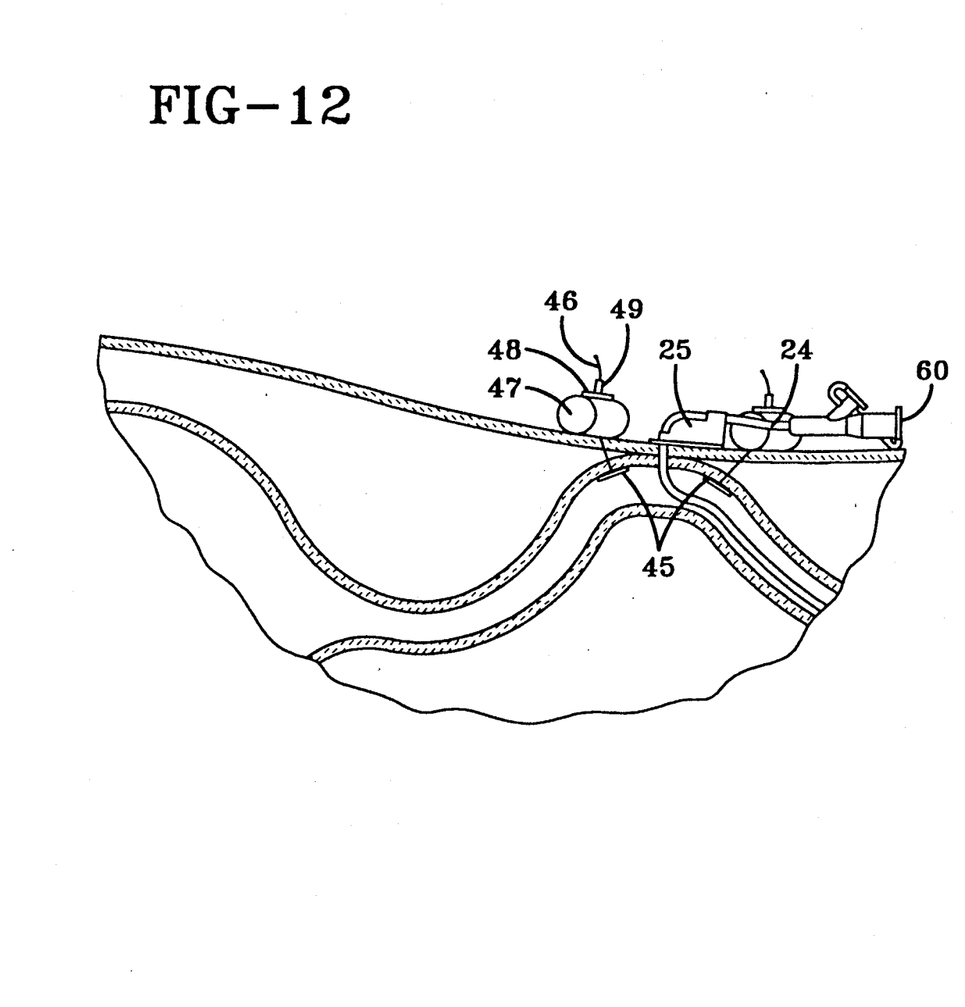
Figure 13:
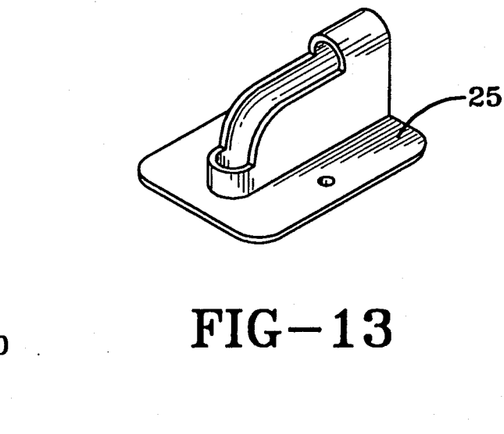
FIGS. 13 and 14 are pictorial representations of two external retaining devices which may be used with a jejunostomy tube.

At this time the surgeon proceeds to create the stoma tract. As shown in FIG. 9, with the jejunum 52 in apposition to the abdominal wall 50 the 18 Ga needle 16 which is attached to an air filled syringe 17 is inserted percutaneously through the center of the T-Fastener square at a 45° angle into the jejunal lumen. Air is injected to confirm placement, and the air should pass easily into the jejunum. Aspiration is performed to further verify correct needle placement, and no blood should appear. The syringe 17 is removed, but the needle is left in place to verify correct needle placement. The J-Guidewire 28 is passed, with the J-hook end 28A first, through the 18 Ga needle distally into the jejunal lumen. The 18 Ga needle is then withdrawn, leaving the J-Guidewire in place. As shown in FIG. 10, the jejunum 52 is dropped by loosening the T-Fasteners 45, 46 slightly to ensure that the J-Guidewire is in the jejunum, then the assistant retightens the T-Fasteners to reapose the jejunum to the abdominal wall. Using the scalpel 15 a small incision is created alongside the J-Guidewire, downward through the subcutaneous layer and the fascia of the abdominal musculature. The assembly of the peel-away sheath 26 and dilator 29 is then passed over the J-Guidewire into the jejunal lumen. That is to say the peel-away sheath 26 has a bore therethrough in which the dilator 29 is inserted, and the dilator has a bore therethrough in which the guidewire 28 is insertable. The dilator and J-Guidewire are then withdrawn and discarded, leaving the peel-away sheath in place. At this time the surgeon 53 proceeds to insert the jejunostomy tube. As shown in FIG. 11, the jejunostomy tube 24 is passed through the peel-away sheath 26, and is guided into the jejunal lumen 52 aiming distally approximately 10 cm beyond the jejunostomy site. The peel-away sheath is then peeled-away from around the jejunostomy tube. The jejunum is temporarily dropped by loosening the T-Fasteners 45, 46 to confirm tube placement laparoscopically 54. After visually confirming appropriate tube placement the T-Fasteners are retightened. The jejunostomy tube can then be tested by injecting saline through the feeding tube side port while the laparoscopist ensures that there is no leakage around the site. To further confirm that tube placement is secure, a radiological examination should be performed by instilling a contrast medium through the jejunostomy tube side port and radiologically checking for extravasation. As shown in FIG. 13 the head of the "T" 45 of each is then stabilized by sliding the nylon washer 48 down against the pledget 47, and crimping the aluminum crimps 49 with a hemostat, then cutting off excess suture 46. The jejunostomy tube 24 is then secured by suturing the external retaining device 25 to the skin. The pneumoperitoneum is then deflated, the laparoscope is removed, and the trocar sites are closed. Although it is possible to feed the patient immediately, it is advisable to wait until the following morning before initiating feedings.

In a preferred embodiment of the jejunostomy instrumentation kit the external retaining device 25 is assembled with the jejunostomy tube and guides the jejunostomy tube through a 90° bend without kinking the jejunostomy tube. The preferred external retaining device 25 has a base which rests against the patient's skin and has holes formed therein to facilitate suturing the retaining device to the person's skin. The external retaining device shown in FIG. 13 guides the jejunostomy through a first hole herein which is aligned with the stoma along a tube guiding conduit which is shaped complementary to the exterior of the tube and guides the tube unkinked through a 90° bend, and a second hole in the device which is oriented substantially parallel to the skin on the patient's abdomen. The two holes in the retaining device through which the jejunostomy tube passes have longitudinal axes which are coplanar and oriented perpendicular to one another. Preferably the hole in the retaining device which is aligned with the stoma has a diameter such that there is a slight interference fit between the retaining device and the jejunostomy tube. There is no interference fit between the device and tube when the tube passes through the hole in the device which is oriented substantially perpendicular to the stoma.

Figure 14:
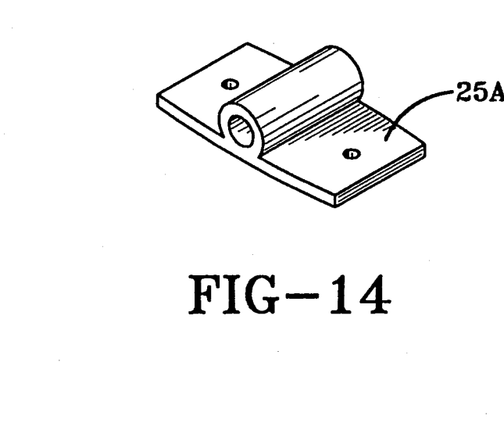

An alternative external retaining device is shown in FIG. 25A, in which the jejunostomy tube passes through the hole in the retaining device. The retaining device is then secured to the patient by sutures placed on one or both wings of the retaining device. This retaining device is not located directly over the stoma. 41

The advantage of maintaining a portion of the jejunostomy tube external of the patient close to the patient's abdomen is to decrease the likelihood of an unplanned removal of the jejunostomy tube by the patient.

The foregoing description is for purposes of illustration, rather than limitation of the scope of protection of this invention. The latter is to be measured by the following claims, which should be interpreted as broadly as the invention permits.

We claim:

1. A laparoscopic jejunostomy instrumentation kit comprising:
 (a) means for securing a patient's intestine in apposition to the patient's abdominal wall;
 (b) means for creating a stoma through the abdominal wall and intestinal wall, wherein said means for creating a stoma comprises a needle, a guidewire which is insertable through a bore in the needle, a peel-away sheath having a bore extending therethrough, and a dilator having a bore extending therethrough, the dilator being insertable through the bore in said peel-away sheath and said guidewire being insertable through the bore in said dilator;

(c) a jejunostomy tube;

(d) an external retaining device which has the capacity to guide the jejunostomy tube through a 90° bend without kinking the jejunostomy tube; and (e) an enclosure for containing the components of the kit.

2. A laparoscopic jejunostomy instrumentation kit according to claim 1 wherein the means for securing the patient's intestine in apposition to the patient's abdominal wall comprises at least three T-Fastener assemblies.

3. A laparoscopic jejunostomy instrumentation kit according to claim 2 wherein the means for securing the patient's intestine in apposition to the patient's abdominal wall further comprises a slotted needle and a stylet insertable therein for placing the T-Fastener assemblies.

4. A laparoscopic jejunostomy instrumentation kit comprising:

(a) at least three T-Fastener assemblies;

(b) a slotted needle and a stylet which is insertable therein for placing the T-Fastener assemblies;

(c) a guidewire;

(d) a peel-away sheath having a bore extending therethrough;

(e) a dilator having a bore extending therethrough, the dilator being insertable through the bore in said peel-away sheath, and said guidewire being insertable through the bore in said dilator;

(f) a jejunostomy tube;

(g) an external retaining device which has the capacity to guide the jejunostomy tube through a 90° bend without kinking the jejunostomy tube; and (h) an enclosure containing the components of the kit.

5. A laparoscopic jejunostomy instrumentation kit comprising:

(a) at least three T-Fastener assemblies;

(b) a slotted needle and a stylet which is insertable therein for placing the T-Fastener assemblies;

(c) a second needle;

(d) a syringe which is attachable to said second needle;

(e) a guidewire which is insertable into a bore through said second needle;

(f) a peel-away sheath having a bore extending therethrough;

(g) a dilator having a bore extending therethrough, the dilator being insertable through the bore in said peel-away sheath, and said guidewire being insertable through the bore in said dilator;

(h) a jejunostomy tube;

(i) an external retaining device which has the capacity to guide the jejunostomy tube through a 90° bend without kinking the jejunostomy tube; and (j) an enclosure containing the components of the kit.

* * * * *

UNITED STATES PATENT AND TRADEMARK OFFICE
CERTIFICATE OF CORRECTION

PATENT NO. : 5,318,543

DATED : June 7, 1994

INVENTOR(S) : J. Ross, M. McCamish, A. Englehart, R. Danis

It is certified that error appears in the above-identified patent and that said Letters Patent is hereby corrected as shown below:

Col. 1, line 49, "turgical" should be --surgical--.

Signed and Sealed this

Fourth Day of October, 1994

Attest:

BRUCE LEHMAN

*Attesting Officer*          *Commissioner of Patents and Trademarks*